United States Patent [19]

Singh et al.

[11] Patent Number: 5,751,416
[45] Date of Patent: May 12, 1998

[54] ANALYTICAL METHOD USING LASER-INDUCED BREAKDOWN SPECTROSCOPY

[75] Inventors: Jagdish P. Singh; Fang-Yu Yueh; Robert L. Cook; Hansheng Zhang, all of Starkville, Miss.

[73] Assignee: Mississippi State University, Mississippi, Miss.

[21] Appl. No.: 705,267

[22] Filed: Aug. 29, 1996

[51] Int. Cl.[6] ............................................. E01J 3/30
[52] U.S. Cl. ......................... 356/311; 356/300; 356/318; 356/417
[58] Field of Search .............................. 356/311, 300, 356/318, 38, 36, 417

[56] References Cited

U.S. PATENT DOCUMENTS

| | | |
|---|---|---|
| 4,561,777 | 12/1985 | Radziemski et al. |
| 4,986,658 | 1/1991 | Kim. |
| 4,993,834 | 2/1991 | Carlhoff et al. |
| 4,995,723 | 2/1991 | Carlhoff et al. |
| 5,091,652 | 2/1992 | Mathies et al. |
| 5,256,852 | 10/1993 | Boudot. |
| 5,446,538 | 8/1995 | Noll ............................ 356/318 |
| 5,469,255 | 11/1995 | Kamada et al. ............. 356/318 |
| 5,608,519 | 3/1997 | Gourloy et al. ............ 356/318 |

OTHER PUBLICATIONS

Chen Yu Huang et al., Preprint Extended Abstract, Presented at the I&EC Special Symposium American Chemical Society, Trace Analysis of Toxic Metals in Air by Lase Induced Breakdown Spectroscopy, 4 pp., Sep. 17–20, 1995.

Jagdish P. Singh et al., Proceedings of the International Symposium on Environmental Technologies: Plasma Systems and Applications, Application to Toxic Metal Concentration Measurements in a Plasma Torch Off–Gas Emission System, Oct. 8–11, 1995, pp. 409–420.

Claus J. Lorenzen et al., Journal of Analytical Atomic Spectrometry, Applications of Laser–induced Emission Spectral Analysis for Industrial Process and Quality Control, Sep. 1992, vol. 7, pp. 1029–1035.

Primary Examiner—Frank G. Font
Assistant Examiner—Reginald A. Ratliff
Attorney, Agent, or Firm—Oblon, Spivak, McClelland, Maier & Neustadt, P.C.

[57] ABSTRACT

The invention relates to an analytical method using laser-induced breakdown spectroscopy.

14 Claims, 2 Drawing Sheets

ANALYTICAL METHOD USING LASER-INDUCED BREAKDOWN SPECTROSCOPY

BACKGROUND OF THE INVENTION

1. Field of the Invention

This invention relates to an analytical method using laser-induced breakdown spectroscopy.

2. Discussion of the Background

Laser-induced breakdown spectroscopy (LIBS) is a laser-based diagnostic technique developed to measure elemental concentrations in a variety of materials (D. A. Cremers et al, "Laser Plasmas for Chemical Analysis" in *Laser Spectroscopy and its Application*, L. J. Radziemski, R. W. Solarz, J. A. Paisner, Eds. (Marcel Dekker, New York, N.Y., 1987), Chap. 5, p. 351, L. J. Radziemski et al, "Spectrochemical Analysis Using Plasma Excitation" in *Laser Induced Plasmas and Applications*, L. J. Radziemski, and D. A. Cremers, Eds. (Marcel Dekker, New York, N.Y., 1989), Chap. 7, pp. 295-326, D. K. Ottesen et al, Energy & Fuels, vol. 5, p. 304 (1991), K. J. Grant et al, Appl. Spectrosc., vol.45, p. 701 (1991), D. K. Ottesen et al, Appl. Spectrosc., vol. 43, p. 967 (1989)). LIBS uses a high power laser to vaporize and excite a sample in one step. In the LIBS technique, a pulsed laser beam is typically focused at a test point to produce a spark. The spark in the focal region, generates a high density plasma which produces and excites various atomic elements in the test volume. Atomic emission from the plasma may be collected with a collimating lens and sent to a detection system. The intensity of the atomic emission lines observed in the LIBS spectrum is then used to infer the concentration of the atomic species. The atomic emissions generated in the laser-produced plasma can be transferred a long distance through optical fibers that provide remote capability for the detection system. LIBS also offers advantages over classical methods, because measurements can be made without time-consuming sample preparation.

LIBS has been used to analyze solids (J. A. Aguilera et al, Appl. Spectrosc., vol. 46, p. 1382 (1992) and Z. W. Hwang et al, Appl. Spectrosc., vol. 45, p. 435 (1991)), liquids (D. A. Cremers et al, Appl. Spectrosc., vol. 38, p. 721 (1984) and J. R. Wachter et al, Appl. Spectrosc., vol. 41, p. 1042 (1987)), gas and aerosol samples (J. P. Singh et al, Application of modern diagnostic methods to environmental improvement: Laser induced breakdown spectroscopy (LIBS) DIAL/MSU, Annual Report, 1994, DIAL 10575, and H. Zhang, Ph.D. Thesis, Mississippi State University, 1994)). LIBS has also been utilized to detect Be, Na, P, As and Hg in air (L. J. Radziemski et al, Anal. Chem., vol. 55, p. 1246 (1983)). The detection limit for Be in air has been reported to be as little as 0.6 ppb. It has also been applied to a harsh, turbulent and highly luminescent coal-fired magnetohydrodynamic gas stream (H. Zhang et al, Appl. Spectrosc., vol. 49, p. 1617 (1995)). It has also been used to measure the various elements in the off-emission of joule-heated vitrification melters (W. L. Flower et al, Proceedings of International Incineration Conference, p. 73 (1994)) and in a plasma torch (J. P. Singh et al, LIBS Measurement at WETO/MSE, DIAL, Mississippi State University, DIAL 10575, Trip Report 94-3).

In addition to analysis of stable isotopes, LIBS has also been used limitedly to detect radioactive material. A sample cell for analyzing numerous Pu samples by LIBS is reported (H. N. Barton, Appl. Spectrosc. Vol. 23, p. 519(1969)). LIBS is used to determine diffusion data and fission product release from coated fuel particles (H. J. Allelein et al, Proc. 1st Eur. Conf. on Optical System and Application, Brighton (1978)). LIBS has been used to measure uranium in solution (J. R. Wachter et al, Appl. Spectrosc. Vol. 41, p. 1042 (1987)). LIBS is preferable to radiological measurements, because nuclear detectors may not be able to differentiate between the radionuclides U, Pu and Np. Thus, chemical separation is required before radiologically analyzing a sample with a nuclear detector.

Toxic metal emissions from various waste processing off-gas systems represent a significant health hazard (R. J. Sullivan, "The Air Pollution Aspects of Arsenic and its Compounds" NAPCA PB-188071 and PB-188075 (September, 1969) and H. B. Dellinger et al, "Evaluation of the Origin, Emissions, and Control of Organic and Metal Compounds from Cement Kilns CoFired with Hazardous Wastes", The Scientific Advisory Board on Cement Kiln Recycling Report, Process Technology Work Group, June 1993). The U.S. Environmental Protection Agency is in the process of imposing more stringent rules which will further reduce the quantities of toxic metals released into the environment. A real-time toxic metal monitoring system is needed to measure the metal concentrations in system off-gases to control the processing system.

To date, only a limited number of studies have been reported which attempt to use LIBS as a quantitative technique. Cremers et al. have pioneered much of the early work on the quantification of Be. (L. J. Radziemski et al, Anal. Chem. vol. 55, p. 1246 (1983)). Quantification of As, B and P as metal hydrides in a He environment has been reported (E.A.P. Cheng et al, Appl. Spectrosc., vol. 45, p. 949 (1991)). The study focused on detection of various hydrides in a He environment for their detection by the semiconductor industry. Stable reference gas mixtures were used to calibrate the technique and derive the limits of detection for each element.

Recently, a mobile and versatile LIBS system has been developed at the Diagnostic Instrumentation and Analysis Laboratory (DIAL), Mississippi State University (MSU) to monitor toxic metal concentrations in the off-emission of a plasma hearth process system. It has been used to measure the concentration of toxic metals in the off-gas from a Savannah River (SR) surrogate vitrified with DIAL's plasma torch facility (J. P. Singh et al, "LIBS: Off-Gas Emission Measurement of Savannah River (SR) Surrogate Vitrification with DIAL/MSU PT-150 Plasma Energy Corporation Torch", DIAL/MSU Trip Report TR 95-3, DIAL 10575 (1995)). Off-gas measurements have also been made at the Western Energy Technology Office (WETO) torch facility / Mountain State Energy (MSE), Montana (J. P. Singh et al, "Plasma Arc Centrifugal Treatment System, Western Environmental Technology Office: LMS Measurements", DIAL/ MSU, Trip Report 94-3, DIAL 10575, pp. 38–53 (1994)). In addition, the performance of this system has been evaluated in the Advanced Analytical Instrumentation Demonstration (AAID) test at Science Applications International Corporation (SAIC)'s STAR Center, Idaho Falls, Id. (R. L. Cook et al, "Advanced Analytical Instrumentation Demonstration—LIBS Measurement", SAIC's STAR Center, Idaho Falls, DIAL/MSU Trip Report 95-1, DIAL 10575 (1995) and C. Cornelison et al, SAIC Report SAIC-95/1308 (1995)).

Lorenze et al, J. Anal. Atom. Spec. Vol. 7, p. 1029 (1992), report the application of Laser-Induced Emission Spectral Analysis, for industrial process and quality control in which a pulsed high-powered laser produces a hot bright plasma and the emission spectra analyzed by conducting the plasma light via an optical fiber bundle, to a spectrometer. The use of such a process to detect elements in an amount between 10–100 ppm from matrices such as steel, rubber, rock and glass is reported. The system is difficult to use in an industrial environment and used a multiplicity of lenses for focussing the laser beam and collimating the LIBS signal.

Carlhoff et al. U.S. Pat. No. 4,559,723, report a method and apparatus for optically coupling an elemental analysis system and a laser to a liquid metal in a melting vessel in which laser light is reflected onto the free surface of a melting bath, and the metal vapor plasma is analyzed. A multilens system is used. Carlhoff et al have used a small laser mirror in place of a dichroic mirror. This mirror is in the LIBS signal path. The following are the disadvantages and problems in this LIBS system. It blocks a part of the LIBS signal generated at the laser focal point. This configuration can't block the reflected laser beam which can burn optical fiber, grating, slit and detector in the detection system. This system has to be very close to the melt which is not practical for glass and steel industries. The temperature near melt glass or steel is very high. This also limits the remote operation of the LIBS system.

Cremers et al, U.S. Pat. No. 4,561,777 report an apparatus and a method for near real-time in situ monitoring of particulates and vapors contained in a fluid, in which the particulate is concentrated on a filter element and the filter analyzed by laser-induced dielectric breakdown spectroscopy, to obtain qualitative and quantitative information. This does not provide for the measurement in real time and can not be used with melt glass or metal.

Kim, U.S. Pat. No. 4,986,658, reports a method and apparatus for spectroscopic analysis of molten metal, in which a probe containing a pulsed-power laser is immersed in a molten metal bath, wherein irradiation vaporizes a portion of the molten metal, to produce a plasma plume, having an elemental composition representative of the elemental composition of the molten metal. The immersed probe system is not easy to use and not suitable in most of the molten metal or glass.

Boudot, U.S. Pat. No. 5,256,852, reports the use of a dichroic mirror in a laser/spectrometer system for simultaneously welding and analyzing the progress of the weld. A Nd:YAG continuous wave (cw) laser is used for welding. The laser damage threshold (power/$cm^2$) is low in cw application. In this application the detector is actually an interferometer rather than a spectrometer. Moreover, the dichroic mirror in this application may not need to reflect all the wavelengths from 200–1000 nm. This application needs only to analyze a few spectral lines, from the welding point. The dichroic mirror used in this application is of a low power damage threshold and reflects only few spectral lines, which is not suitable to be used in a LIBS system.

Mathies, U.S. Pat. No. 5,091,652, reports the use of a dichroic beam splitter in conducting laser analysis of DNA fragments on a gel. In the fluorescence technique requires very low laser power. The laser power in fluorescence is $10^3$–$10^6$ times lower than that of LIBS. In the fluorescence technique both pulsed and continuous wave (cw) lasers are used. A dichroic mirror of low damage threshold can be used for cw laser application. The typical damage threshold of this type of DM is ~$10^3$ watts/$cm^2$ whereas in LIBS damage threshold is ~$100 \times 10^6$ watts/$cm^2$ which is ~$10^5$ times higher. In this application, either lower wavelength or higher wavelength transmission are required. The appropriate term for this dichroic mirror is low wave pass and high wave pass filter. This type of filter or so called dichroic mirror by Mathies et al, cannot be used in LIBS applications.

Carlhoff DE 4,410,398, reports a method of polymer material identification in the sorting of plastics, using a pulsed laser to generate plasma, thereby identifying the polymeric material by the emission spectrum.

Carlhoff EP 652,430, reports the use of pulsed laser beam generated plasma for measuring the concentration of carbon black in rubber compounds.

Carlhoff DE 4,138,157, reports the use of pulsed lasers to generate plasma in measuring the thickness of zinc coatings on steel.

Carlhoff EP 392,337, reports the use of spectral line intensity ratios of material plasma in determining material constituent concentration ratios. This process is indicated as useful for the analysis of solids, liquids or gaseous materials especially molten alloy steels.

Present designs of LIBS systems, carries certain deficiencies which can be improved upon.

Accordingly, improved methods and apparatuses for conducting laser-induced breakdown spectroscopy are being sought.

The inventors of the present invention have developed a LIBS system which is a versatile system which overcomes most of the deficiencies in the previous systems. The LIBS optical probe has an unique design for practical application. A single lens is used to focus the laser beam and also to collect the LIBS signal. This LIBS system is suitable for industrial environmental which has limited access to measurement area.

A specially coated dichroic mirror (DM) is an unique optical element of the system which is needed for molten glass and metal applications. The special coating was developed with the help of CVI Laser Corporation, New Mexico, and reflects at 532 nm at an angle of 45° and transmits 180–510 nm and 550–1000 nm. The coating damage threshold >$100 \times 106^6$ watts/$cm^2$ at 532 nm laser beam. The LIBS optical system with a DM is particularly useful in molten glass and metal applications to reduce the reflected light from the test medium. The reflected laser light can burn optical fiber, grating, slit or detection system. Thus the LIBS optical system presented here is unique, versatile and free from most of the problem in the previously reported system.

SUMMARY OF THE INVENTION

Accordingly, one aspect of the present invention is directed to a novel apparatus for conducting laser-induced breakdown spectroscopy.

Another embodiment of the present invention is directed to a method of analyzing the composition of a material using laser-induced breakdown spectroscopy.

According to another aspect of the present invention, is directed to a method of qualitatively and quantitatively measuring the concentration of radioactive elements in a sample.

According to another embodiment of the present invention, is directed to a method of detecting toxic metals in off-gas emission.

According to another embodiment of the present invention, is directed to a method of monitoring a process by monitoring elemental concentrations of inputs and/or outputs from a process.

These and other objects of the present invention are made possible by a laser-induced breakdown spectroscopy apparatus in which laser light is directed to a sample via a specially coated dichroic mirror and a focusing lens, wherein an emission spectrum is directed via said focusing lens, through said dichroic mirror to a spectrometer.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

A pulsed laser (1) of almost any type can be used to generate a laser spark. Suitable non-limiting examples include $CO_2$, excimer krypton fluoride, neodymium yttrium-aluminum garnet (Nd:YAG), ruby, titanium sapphire, aluminum gallium arsenide, indium gallium arsenide phosphide, aluminum indium gallium phosphide, and various dye lasers.

Laser light of any wavelength and frequency, sufficient to vaporize and excite a sample may be used. Selection of a suitable wavelength and frequency, as well as the intensity, is within the level of skill of one of ordinary skill in the art.

The intensity of the laser pulse may be adjusted to be sufficient to generate a laser spark. A light source which has a power density above the breakdown threshold of the test medium can be used in LIBS measurement. Although different test media have different breakdown threshold values, a laser-induced plasma is typically generated when the laser power density is over 1 $GW/cm^2$.

The frequency of the laser pulse is not particularly limited. Suitable frequencies range from 5 to 30 Hz, preferably about 10 Hz. For example, when the sample to be analyzed is molten glass the frequency is about 10 Hz.

The duration of a laser pulse, is sufficient to generate a laser spark. Suitable pulse durations are generally 5–15 n sec.

For safety purposes, it is preferable to have a light source in the visible region. The Nd:YAG (1.06 μm) laser can be frequency-doubled to 532 nm by using a doubling crystal of the KDP Type I. Devices for frequency-doubling laser light are conventionally known to those of ordinary skill in the art.

Figure 1:
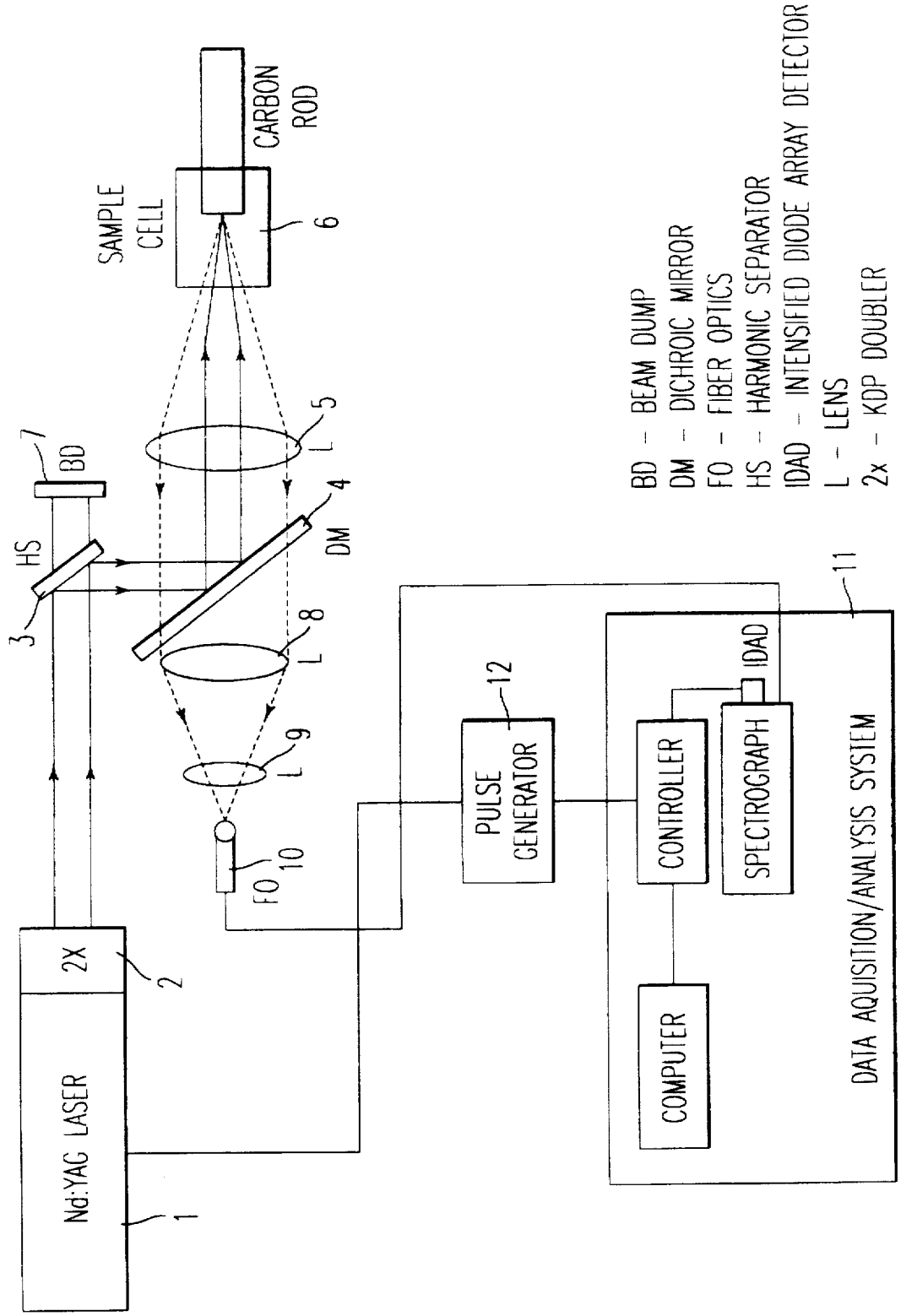
FIG. 1 provides a schematic representation of an apparatus for conducting LIBS on a solid sample.

A system of a harmonic separator, a dichroic mirror and a focusing lens are used to direct the laser light to the site of analysis as shown in FIG. 1.

The harmonic separator (3) is used to separate frequency doubled laser light from a fundamental or main laser beam in the laser industry. It reflects the frequency doubled laser beam and passes the fundamental laser beam to a beam dump (7).

The dichroic mirror (4) is a dielectric coated mirror which is equipped with an anti-reflective coating to reflect high energy pulsed laser beams, but transmits other wavelengths especially those of the emission spectrum. The transmission of a standard DM is only up to 240 nm. Accordingly, when frequency doubled Nd:YAG laser light is used a special coating on the dichroic mirror is used which can transmit up to 180 nm and reflect 532 nm which is frequency doubled Nd:YAG laser beams. The DM also preferably has a damage threshold of >100×$10^6$ watts/$cm^2$ and transmits a frequency of 180–1,000 nm, except at the laser wavelength. The laser wavelength band width for reflection at the laser wavelength should be about 40 nm, preferably centered around the laser wavelength. Accordingly, a suitable dichroic mirror has a band transmission frequency, but is equipped with a "mask" of about 40 nm, near the laser wavelength.

The dichroic mirror is able to reflect frequency doubled laser light onto the sample to be analyzed and transmit light from the spark to a detector. Because the dichroic mirror is reflective of the laser light, laser light which is reflected or scattered from the sample is not transmitted to the detector. In other words, the same reflective properties of the dichroic mirror which allow laser light to be directed onto a sample, also reflects laser light which has been reflected from the sample. This simple design protects the detector from the potentially damaging reflected laser light.

The coating material used for excimer lasers dichroic mirror for reflection at 190–248 nm was tested for high power damage threshold at 532 nm. This coating was modified to reflect 532 nm. The excimer laser DM coating transmits down to 180 nm as compared to 240 nm for a standard 532 nm DM.

The properties of the dichroic mirror to transmit light from the spark (i.e. an emission spectrum) is independent of the incident angle of the light from the spark. This allows for flexible arrangement of the reflective positioning of the laser source and detector relative to the sample. In a preferred embodiment, the dichroic mirror is situated at a 45° angle relative to a line between said detector and sample.

A special type of dichroic mirror is a harmonic separator. A unique part of the present invention is a specially coated dichroic mirror.

A focusing lens is used to focus the laser beam onto the sample and to collect light from the induced laser spark and pass it through to the dichroic mirror. A suitable focussing lens is an ultraviolet (UV) grade quartz lens which allows the emission line in UV regions to reach the detection system. A suitable focussing lens will have a focal length sufficient to direct the laser beam on to the sample surface, sufficient to induce a laser spark and accordingly the focal length will vary depending on the dimensions of the apparatus. Typically the focal length of the focussing lens will be from 100–1,000 mm, preferably 100 mm for off-gas emission and 500 mm for melt glass.

When a sample (6) is vaporized, atomic emissions from the sample are collected, which are to be analyzed.

It is preferable for the emission spectrum to be transmitted via focusing lens (5), and separated from the laser light through the dichroic mirror (4), before being directed to the detector (11). In this fashion, the emission spectrum is transmitted to the detector, but laser light which is reflected from the sample is reflected away from the detector.

It is also preferable, that the emission spectrum, after it has been focused, to be directed to the detector, via a fiber optic link (10), since this provides remote detection of the spectrum. However, direct detection of the emission spectrum, without a fiber optic link, is within the scope of the present invention. Suitable fiber optic means are well known to those of ordinary skill in the art. For example, a suitable fiber optics bundle cable may have a core diameter of 0.05–0.2 mm, preferably 0.1 mm, and a numerical aperture (NA) of the bundle matching the F# of the spectrometer.

The emission spectrum may be analyzed via a detector such as an optical spectrograph such as Model HR 460, from Instruments SA Inc, Edison N.J. Any detector capable of qualitative analyses of an emission spectrum, may be used. Such detectors are known to those of ordinary skill in the art. The exit end of the fiber optic cable may be fed directly into the entrance slit of the spectrograph.

The spectrometer may be equipped with 1200 and 2400-lines/mm diffraction gratings of dimensions 75 mm×75 mm. The 2400-lines/mm diffraction grating may be used in this experiment. A 1024-element intensified diode array detector (Model IDAD-1024, Princeton Applied Research Corp., Princeton, N.J.) with a pixel width of 0.022 mm may be used to detect the light from the laser spark. The detector may be used in the gated mode and can be synchronized to the laser output. A gate width of 20–40 µs may be used. The gate pulse delay may be varied in the range between 5 and 30 µs to achieve the best signal-to-background ratio. With a 2400-lines/mm grating, the spectral window monitored by the array was ~19 nm with a resolution of 0.16 nm. Data acquisition and analysis may be performed using a notebook computer. An ICCD detector and other computer systems can also be used to replace an IDAD detector and notebook computer.

The emission spectrum is analyzed to provide qualitative and/or quantitative data as to the composition being tested.

The LIBS method according to the present invention can be used to measure such compositions as molten glass, melt slag/glass effluent, from various waste thermal processing facilities, molten slag from a precious metal recovery plant, solid products from thermal treatment facilities and from metal industries, slurry/liquid feeds from various industrial processes.

The present invention can also be used to measure the concentration of radioactive elements (radionuclides) in matrices such as glass/slag, melt glass/slag, and off-emission gas from a waste thermal treatment facility.

LIBS can also be used as a process monitor and control, by monitoring the elemental concentrations of the feed and products for various waste treatment facilities both radioactive and non-radioactive, metal industry processing facilities and glass manufacturing facilities. The process can also be used to measure toxic metals and radioactive elements in water, food products and from suspected contamination areas. An instrument useful for process control would use a LIBS detection apparatus as described above, and in conjunction with the information obtained from the LIBS detection apparatus, modify the process parameters as necessary to obtain the desired process results. Accordingly, the necessary components of an instrument for process control will depend on the nature of the process being monitored and the adjustments that can be made to the system. The application of the qualitative and quantitative information obtained by a LIBS technique may be applied to a process monitoring system by those of ordinary skill in the art.

Having generally described this invention, a further understanding can be obtained by reference to certain specific examples which are provided herein for purposes of illustration only and are not intended to be limiting unless otherwise specified.

EXAMPLE 1

A. LIBS Instrument

Details of the experimental arrangement of the LIBS system are described in J. P. Singh, H. Zhang, F. Y. Yueh and K. P. Carney, Appl. Spectrosc. Vol. 50, p 764 (1996), and are shown in FIG. 1.

In brief, the output (1064 nm) of a Nd:YAG laser (Surelite I, Continuum) was frequency-doubled to 532 nm using a doubling crystal (KDP Type I). A dichroic mirror was used to separate the frequency-doubled output from its fundamental frequency. An ultraviolet (UV)-grade quartz lens was used to focus the laser beam. The same lens was used to collect light from the induced laser spark. Two UV grade quartz lenses were used to couple the LIBS signal to an optical fiber bundle. The other end of the fiber bundle was coupled to an optical spectrometer (Model HR460, Instruments SA Inc, Edison, N.J.). The entrance slit of the spectrograph was replaced by the rectangular exit end of the optical fiber. The spectrometer was equipped with 1200 and 2400-lines/mm diffraction gratings of dimensions 75 mm×75 mm. The 2400-lines/mm diffraction grating was used in this experiment. A 1024-element intensified diode array detector (Model IDAD-1024, Princeton Applied Research Corp., Princeton, N.J.) with a pixel width of 0.022 mm was used to detect the light from the laser spark. The detector was used in the gated mode and was synchronized to the laser output. A gate width of 20 µs was used in this work. The gate pulse delay was varied in the range between 5 and 20 µs to achieve the best signal-to-background ratio. With a 2400-lines/mm grating, the spectral window monitored by the array was ~19 nm with a resolution of 0.16 nm. Data acquisition and analysis were performed using a notebook computer (Model T-4700CS, Toshiba).

B. Glove Box interface

To perform LIBS measurements on a radioactive sample, a glove box may be required to avoid the problem of containment. The glove box facility at Argonne National Laboratory—West was used in this study. The glovebox was modified to adapt to the LIBS system. A CRL glove port blank with 2-in. quartz view port (MDC corporation) was glued with RTV silicon adhesive to the glove box. A sample cell, made of a 4-in. long MDC double flange nipple and an MDC 2.75-in. conflat blank flange was attached to the glove box port from inside. A ¼-20 nylon screw was attached with a spectroscopic gate carbon rod and passed through the MDC conflat blank flange. This nylon screw was loosely attached to the flange so that it can be rotated. The tip of the carbon rod was used to deposit the sample.

C. Sample Preparation

Solution samples of Pu and Np inside a glove box were doped with a 0.1-ml pipette onto the tip of the carbon rod. The concentration of the sample solution was 10,000 µg/ml. A 50-µl drop of solution was evaporated on the surface of the rod for each LIBS measurement. The sample can be rotated during the LIBS spectrum recording by rotating the nylon screw. A 100-µl drop of U-238 solution from Spex Industries was dried on the tip of the carbon rod for the U measurement. The concentration of the U sample solution was 10,000 µg/ml.

Standard 1,000-µg/ml uranium solution (AccuStandard) was diluted and used to record the LIBS spectra at different concentrations. The U sample from an ultrasonic nebulizer (CETEC AT 5000) was injected into the air through a 7-mm inner diameter (I.D.) stainless steel tube enclosed in a 15-cm I.D. plexiglass pipe attached to an exhaust system. The air flow rate was 700 cc/sec. The efficiency of the nebulizer was measured by the LIBS system and found to be 19%.

RESULTS

The LIBS spectra of U, Np and Pu solutions were recorded in various spectral regions to determine the most sensitive lines of each element. Table I shows the emission lines of the impurities observed in each sample measurement. The most sensitive lines of Pu, Np and U found in the various spectral regions are listed in Table II.

TABLE I

The observed emission lines from the impurities.

| Sample | Impurity | Wavelength (nm) |
|---|---|---|
| Np | Ca | 393.37, 396.847, 422.673 |
|  | Si | 250.69, 251.43, 251.61, 251.92, 252.41, |

TABLE I-continued

The observed emission lines from the impurities.

| Sample | Impurity | Wavelength (nm) |
|---|---|---|
|  |  | 252.85, 263.13 |
|  | Al |  |
| Pu | Ca | 393.37, 396.85, 422.673 |
|  | Al | 394.4ª, 396.152ª |
|  | Fe | 407.13, 413.206, 414.38, 420.20, 423.75, 425.08 |
|  | Si | 250.69, 251.43, 251.61, 251.92, 252.41, 252.85, 263.13 |
| U | Ca | 422.673 |

ªIntensity of this line is weak.

TABLE II

The suitable lines for detection of U, Pu and Np by LIBS in various spectral regions.

| Element | Spectral Regions | Delay Time (μs) | Emission Line (in nm) | Intensity (Counts) |
|---|---|---|---|---|
| Np | 453 nm | 5 | 456.087 | 861,126 |
|  | 416 nm | 5 | 410.834 | 688,271 |
|  | 397 nm | 10 | 399.69 | 809,207 |
|  | 359 nm | 10 | 360.702 | 491,657 |
|  | 378 nm | 10 | 370.824 | 615,283 |
|  | 260 nm | 10 | 265.506 | 50,867 |
| Pu | 453 nm | 2 | 453.63 | 364,365 |
|  | 416 nm | 20 | 415.96 | 67,796 |
|  | 397 nm | 5 | 398.56 | 48,642 |
|  | 359 nm | 5 | 363.22 | 89,607 |
|  | 260 nm | 5 | 261.86 | 3,311 |
| U | 416 nm | 10 | 409.013 | 307,791 |
|  |  |  | 411.61 | 173,248 |
|  |  |  | 417.16 | 158,747 |

The strongest lines of these three elements in this study are due to ions. The most sensitive U lines in the 407–426 nm spectral region are the U 409.013 nm, 411.61 nm, 417.16 nm and 424.17 nm lines. The strongest Np and Pu lines are in the spectral region of 444–463 nm. The Np 456.05 nm line and Pu 453.62 nm line can be used to detect Np and Pu, respectively.

LIBS spectra from U aerosol were recorded in the spectral region of 395–414 nm to determine the detection limit of uranium.

Uranium solutions of various concentrations were used to produce aerosols of different U concentrations using air as a carrier gas. A calibration curve was determined for the U 409.013 nm line. A delay time of 30 μs and a gate width of 40 μs were used for these measurements. Calibration curves for both line area and line peak height were obtained. The LOD is estimated using the following formula (Edelson et al, "Analytical Atomic Spectroscopy of Plutonium - I. High Resolution Spectra of Plutonium Emitted in an Inductively Coupled Plasma," (Spectrochim Acta, Vol. 41B, P#475 (1986)).

$$LOD = 3 \cdot \sigma \cdot C_o / I$$

where $\sigma$ is the standard deviation of the background signal, $C_o$ is the solution concentration of the analyte, and I is the intensity of the analyte line. In this study, the detection limit of uranium was found to be 1.4 μg/ml (i.e., 1.359 μg/scm) based on the peak height calibration. The mass flow rate of air and nebulizer efficiency was taken into account in the calculation.

The most sensitive N, Pu and U lines for detection of these radionuclides by LIBS were determined. The detection limits of U were also estimated. The hyperfine, or isotopic, splittings of Np and Pu lines were not resolved with the current LIBS system.

EXAMPLE 2

(Abstract only)

Figure 2:
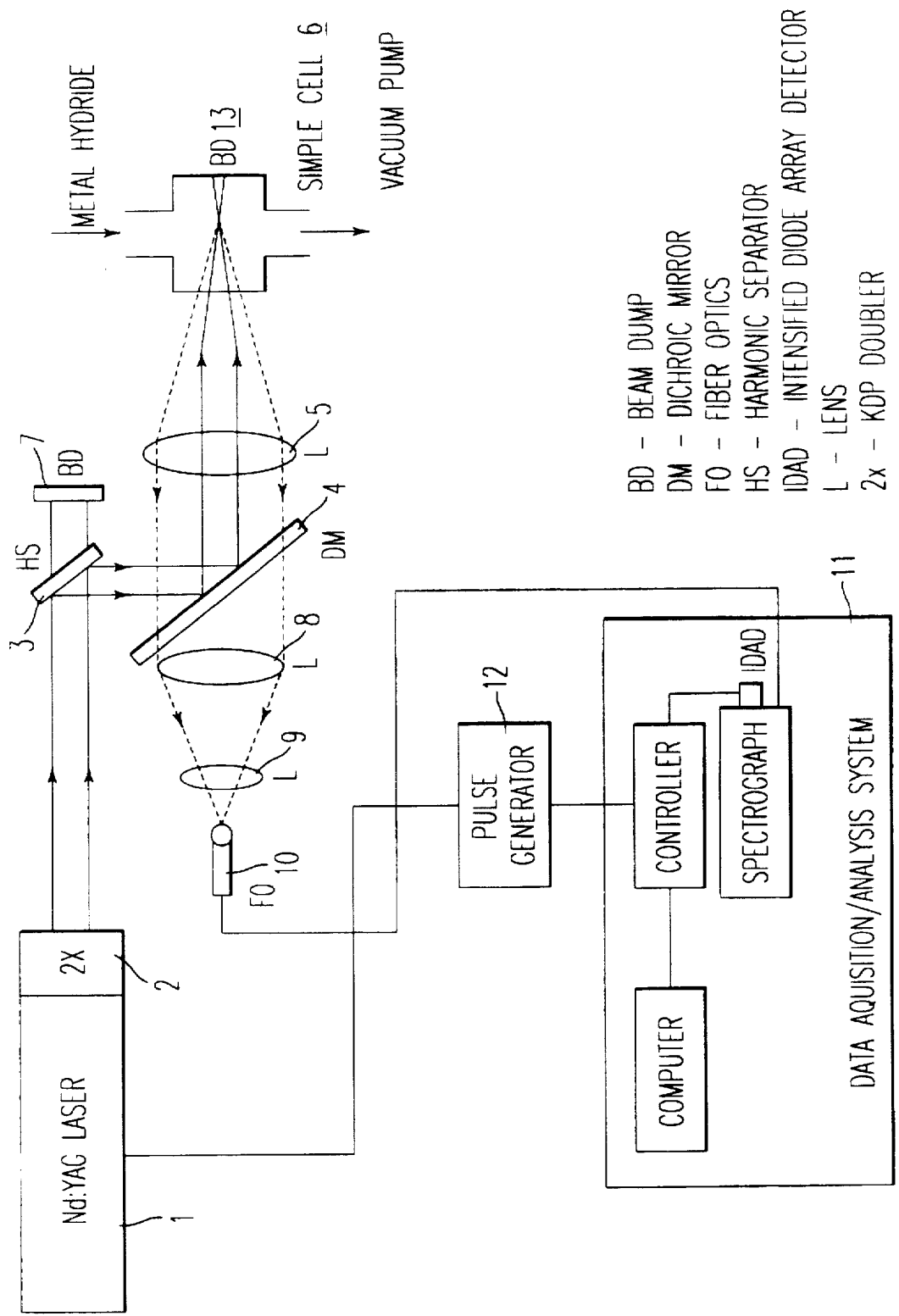
FIG. 2 provides a schematic representation of an apparatus for conducting LIBS on a gaseous sample.

The generation and excitation of metal hydrides in this experiment were performed in spatially segregated vessels. The measurement cell is shown in FIG. 2. A three-armed glass flask was used as a reaction vessel for the generation of volatile hydrides. The hydrides were generated using a $NaBH_4$ reduction reaction which has been described in the literature (R. E. Sturgeon et al, Spectrochim. Acta Vol. 44B, p. 667 (1989), T. Nakahara, Spectrochim. Acta Rev., vol. 14, p. 95 (1991), Y. Madrid et al, Analyst, vol. 119, p. 1647 (1994) and K. Dittrich et al, Analyst vol. 111, p. 269 (1986)). A typical gas pressure of one atmosphere has been used in most of the experiments. The two cells were allowed to equilibrate for approximately 10 minutes; then the cells were isolated and the measurement cell adjusted to the desired measurement pressure using the appropriate gas.

The LIBS spectra of Sn and As hydrides were recorded as a function of time, at different He and $N_2$ gas pressures to study the stability of the hydride and to optimize the experimental conditions to collect data. All data were repeated at least five times with new hydride samples to confirm the reproducibility of the observation.

LIBS spectra of various metal hydrides in the presence of different gases have been recorded. To study LIBS spectra using a hydride generator, the LIBS signal of 7.5 ppm Sn was recorded continuously. Variation of the Sn signal as a function of time, for a period of 30 minutes are recorded. The Sn signal is obtained by subtracting the plasma background. Initially, the signal is maximum and nearly constant for about 60 sec and then starts decreasing. The observed decay curve is nearly exponential. The plasma background has a very similar trend as the Sn signal in the beginning. The rate of decrease in the background is slower than that of the Sn signal.

To study the metal hydride LIBS spectra in another gas mixture, 7.5 ppm Sn spectra were recorded in the presence of He at 760 torr. There are few He lines observed in this spectral region. At 760 torr, the background from the plasma near the Sn emission line at 284.0 nm is 3.4 times lower than the equivalent spectra in $N_2$ gas. The signal is also increased by 1.9 times. The signal-to-background (S/B) ratio in He is ~6.5 times higher than in $N_2$ at 760 torr. However, the signal-to-noise ratio (SNR) in the LIBS emission lines is ~2.5 times higher in the spectra of He than in $N_2$. To study the effect of He gas pressure, Sn spectra at 300 torr have also been recorded. The plasma background is nearly zero. It was observed that the laser spark is more difficult to produce at low He pressure than in $N_2$ with the same laser intensity.

To study the effect of laser intensity on the signal variation, the signal was recorded with different focal length lenses and different laser powers. The Sn signal (284 nm) variation with time in the presence of $N_2$ for three different focal length lenses was determined. These measurements were performed with 200 mJ pulse energy, 50 ppm stannate or tin hydrides, and 760 torr $N_2$ pressure. The signal with shorter focal length lenses (higher intensity) is higher and also decays faster as compared with that from longer focal length lenses.

The Sn signal variation at different laser powers is also determined. The signals were recorded with a 200 mm focal length lens at 760 torr $N_2$ pressure. In the beginning, the signal is higher at higher laser pulse energy. At higher energy it decays faster and decreases to a lower signal at later times (after 300 sec).

The stability of the metal hydride can be estimated from the signal variation with time under different conditions. The Sn LIBS signal in the presence of $N_2$ is fairly constant in the initial 50 seconds. Then it decreases exponentially. The signal decay is due to a process which reduces the concentration of metal hydride in the laser focal volume. Since the signal recorded after 400 seconds continuous spark excitation and the signal recorded with 400 seconds laser spark excitation following a 20 minute delay with no spark excitation are the same. This shows that the LIBS signal has not recovered after a delay time that is sufficiently long to cool and diffuse the gas in the focal volume. Although the diffusion is quite slow in a steady gas sample cell, 20 minutes time is more than enough to diffuse the gas from focal volume of approximately $1.4 \times 10^{-6}$ cm$^3$. Thus the process during laser spark excitation which is responsible for decay of the signal is not confined to the focal volume. This process is throughout the sample cell rather than present only in the focal volume.

The variation of the signal with time in the presence of He is quite different than in $N_2$. The time for the Sn signal to reach the maximum intensity is much longer in He than in $N_2$. The decay of the signal in He after 400 seconds is similar to that in the presence of $N_2$. The longer time required to reach the maximum signal in He might be due to the longer time needed to form a steady plasma in He than in $N_2$. The diffusion rate of He is 2.65 times higher than that of $N_2$ at normal temperature and pressure. Therefore, the electrons generated in the pre-breakdown state could be easily lost by diffusion out of the breakdown volume. Elastic collisions of electrons with neutral He atoms can also contribute to the electron loss in the focal volume during the plasma evolution process, since a He breakdown is difficult to produce due to its high breakdown threshold. The time needed to compensate for this loss might correspond to the time required to reach a steady signal. The characteristic time for plasma avalanche development is different for different elements. As shown in the case of arsine, the increase of the As signal has a different slope as compared to that of Sn.

The study of the temporal variation of the signal shows that the signal is time dependent. It is uniform only during a certain time period. This time period is 10 times longer in He than in $N_2$. The signal is reproducible with new samples for a particular experimental setup and experimental conditions. Various experimental studies on the mechanisms involved in the signal variation show that the signal lifetime is higher at higher sample concentration and lower laser intensity. These observations show that the metal hydride concentration in the sample decreases and this may be due to chemical reactions in the presence of laser-produced plasma.

Further details of LIBS-MH study is described in J. P. Singh, M. Zhang, F. Y. Yueh and K. P. Carney, Appl. Spectrosc., Vol. 50, p. 764 (1996). The various results can be summarized as follows.

Experimental studies of the metal hydrides show that the LIBS signal intensity for a metal hydride changes with time. The signal intensity variation has found quite different in the presence of $N_2$ and of He. The pressure and laser energy used in the experiment will influence the plasma formed and hence change the signal variation characteristics. The time duration at which the signal is maximum depends on the concentration of the sample. The study of the LIBS signal using a metal hydride generator shows some interesting chemical processes which may be responsible for the variation of the intensity of the LIBS signal. This study also concluded that the selection of the time period for the LIBS calibration measurement is an important parameter which affects the calibration of the LIBS system with a metal hydride. This suggests that a flowing metal hydride sample cell system will be better for calibration in order to avoid most of the problems associated with static systems.

EXAMPLE 3

The DIAL/LIBS system has been used at three waste treatment facilities to monitor the concentration of toxic metals in the off-gas system. The broad vibrational peaks due to CN were observed in the spectra recorded at these three facilities. CN is produced from the reaction of C and N which are produced in the spark. The intensity of the CN peaks depends on the concentration of C-compounds (cpds) in the gas stream. The LIBS spectrum in this spectral region is dominated by CN. The CN interference reduces the sensitivity of the LIBS signal for some of the elements.

The DIAL/LIBS system has been calibrated with a hydride generator and a nebulizer system. For the WETO/MSE and DIAL torch LIBS measurements, the data were evaluated with a calibration based on the Sn hydride generator.(J. P. Singh, H. Zhang, F. Y. Yueh and K. P. Carney "Investigation of the Effects of Atmospheric Conditions on the Quantification of Metal Hydrides Using Laser Induced Breakdown Spectroscopy", Appl. Spectrosc. Vol.50,p. 764 (1995) and H. Zhang, J. P. Singh and F. Y. Yueh, "Comparison of Calibration Method for Quantitative Metal Concentration Measurement Using Laser Induced Breakdown Spectroscopy", Anal. Chem. 1996 To be published). The individual element concentrations were calculated using experimental element intensity ratios and taking into account the response function of the detection system and the spectroscopic intensity parameters. The data analysis was based on the peak area of the analyte line. The SAIC's STAR Center LIBS data were calibrated with a nebulizer system using known concentrations of the elements to be detected. The on-site calibration were performed at the STAR Center before the plasma torch test run started with a nebulizer (R. L. Cook, J. P. Singh, H. Zhang, F. Y. Yueh and M. McCarthy, "Advanced Analytical Instrumentation Demonstration—LIBS Measurement", SAIC's STAR Center, Idaho Falls, DIAL/MSU Trip Report 95-1, DIAL 10575 (1995)). The calibration was performed with Cr everyday before the test run to verify the system's alignment. The results from each facility were analyzed and used to evaluate the LIBS system as a process control. The results of some of the measurements are described in the following.

A. WETO/MSBE Measurements

LIBS spectra were recorded in various spectral regions during the three segment test runs on the WETO/MSE Plasma Arc Centrifugal Treatment (PACT) System in October, 1994. The LIBS off-gas heavy metal detection measurements were performed at an optical port located before the baghouse. Special attention was given to the spectral regions with Fe, Cr, Ni and Ce atomic transitions. The elements present in the off-gas were identified from the recorded spectra. The strong Cr lines were found in the spectral regions of 431 nm and 359 nm. There are some Fe lines nearby the Cr lines. The relative concentration of Cr and Fe can be inferred from these two spectral regions using the intensity ratio of the lines. The spectra at 431 nm were recorded 2 minute after the 359 nm spectra. The results from these two spectral regions are in reasonable agreement.

In most cases, 20 LIBS spectra were collected. To compare the measurements with different sample numbers, 100 spectra were also recorded with the same experimental setup in the same spectral regions. The histogram from these two measurement samples are compared. The distribution of the 100 sample data are more close to a Gaussian distribution than the 20 sample measurements. However, the mean value and the standard deviation of these two sets of measurements are very close. The concentration of Cr can be readily compared in the three segment runs using the data collected with the same experimental setup. The intensity of the Cr (428.98) nm line is used to infer the concentration of Cr employing the metal hydride calibration curve. The Cr concentration increased by a factor of four during the segment I feed test from October 17th to 18th. This unexpected results is probably due to non-uniform feed. In general, the concentration of Cr was found to decrease from segment I to segment III. Also the Cr concentration decreases during pouring (no feed) as expected. Note that it takes time to reach a metal concentration of zero after shutdown of the feed. A strong C line at 247.86 nm was also identified from the observed LIBS spectra. This line has been used to monitor the C concentration under different run conditions. The carbon concentration was found to decrease two times from segment I to segment II. The Na concentration in the different run segments was monitored using Na D lines. The intensities of Na D lines slightly increased from segment II to segment III (less than 20%). Since the Na concentration in the feed is 4 times higher in segment III than that in segment II, this measurement shows that most of the sodium remained in the melt and was not going downstream.

The various measurements at WETO/MSE show that LIBS can be used to provide useful information on the operation of the plasma torch, and the off-gas system. It can also provide information about toxic metals or other elemental partitioning during the waste treatment process.

B. DIAL/MSU Plasma Torch Measurement

The heart of the DIAL plasma hearth facility is a 250 kW Plasma Energy Corporation, PT-150 plasma torch. The details of the facility are described in J. P. Singh, H. Zhang and F. Y. Yueh, "LIBS: Off-Gas Emission Measurement of Savannah River (SR) Surrogate Vitrification with DIAL/MSU PT-150 Plasma Energy Corporation Torch", DIAL/MSU Trip Report TR 95-3, DIAL 10575 (1995) and A. L. Kielpinski, J. C. Marra, R. F. Schumacher, J. Congdon, J. Etheridize and R. Kirkland, "Testing of Refractory Materials for Plasma Vitrification of Low-Level Mixed Wastes", in Proceedings of Waste Management '95 Symposium, Tucson, Ariz., Feb. 26—Mar. 2, 1995). The plasma torch was operated in the transferred mode with air as the plasma medium. The hearth was a small graphite container of 30 cm inner diameter and 23 cm height. The LIBS measurements were performed at an optical port located 112 cm from the plasma torch chamber.

Tests at DIAL on the WSRC surrogate feed were performed in March, 1995 to determine the lifetime of various refractory materials. The simulated feed in a briquette form was fed into the torch hearth for vitrification. The feed material composition can be found in (A. L. Kielpinski; J. C. Marra, R. F. Schumacher, J. Congdon, J. Etheridize and R. Kirkland, "Testing of Refractory Materials for Plasma Vitrification of Low-Level Mixed Wastes", in Proceedings of Waste Management '95 Symposium, Tucson, Ariz., Feb. 26–Mar. 2, 1995).

The elements present in the off-gas just downstream of the graphite crucible were identified as Al, B, C, Ca, Ce, Cd, Cr, Cs, Fe, K, Mg, Mn, Na, Pb, Si, Ti, Y, and Zr from the LIBS spectra recorded at various spectral regions during the various SR surrogate test runs. It should be noted that various refractory materials were initially placed in the graphite crucible to study their durability under vitrification with the surrogate waste. Special attention was given to the spectral regions with Pb, Cr, Cd, and Cs atomic transitions. The LIBS spectra were also collected continuously to study the variation of metal concentration with time. The typical data integration period for this test is 3.5 seconds. Generally, the metal concentration increases right after new feed was added to the plasma torch. Therefore, the metal concentration remains nearly constant for a few minutes and then started decreasing. However, this also depends on the arc attachment point in the melt glass which is quite random. The concentration ratios of various metals have also been monitored with time.

Three Cd lines near the 361 nm spectral region were observed in most of the recorded spectra. However, it is difficult to obtain reliable concentrations from those lines due to the poor signal-to-noise. Cs-137 is a radioactive element which is of concern in the treatment of DOE mixed waste. Concentration measurements of Cs-137 can be useful in process control. A Cs-137 line at 852.12 nm was observed during these test runs. The Cs concentrations were found to be rather constant during the various tests.

LIBS spectra were also recorded during the shutdown of the torch on March 8 to monitor the variation of the concentration of Pb and Fe during this shutdown process. The concentration of Pb and Fe dropped rapidly at the moment the current was shut off. Since the glass and crucible are still hot for some time after the torch is shut off, this shows that much of the metal volatilization is due to the high localized heating of the plasma arc. These observations are consistent with those obtained by the emission of voltroscopy to monitor the emission of volatile species in the plasma torch chamber during these experiments.(P. R. Jang et al, "Pyrometry Studies of Mixed Waste Vitrification Plasma Arc Centrifugal Treatment System", Proceedings of the Third Biennial Mixed Waste Symposium, Baltimore, Md., Aug. 7–11, 1995 (A. A. Maghissi et al.) (Cognizant Communication Corp. New York, 1995), pp. 8.2.1–.2.9.)

C. SAIC's STAR Center Measurement

The DIAL/LIBS system was employed for near real-time monitoring of toxic metal concentrations during a week-long test at SAIC's STAR Center. The STAR Center plasma system consists of the following components: plasma chamber, secondary combustion chamber; baghouse; HEPA filter, stack; and instrumentation and system control. The details of the STAR Center's facility are described in (C. Cornelison et al, "Final Report for the Advanced Analytical Instrumentation Demonstration", SAIC/MSE, SAIC Report SAIC-95/1308 (1995)). Two waste types were processed during the tests: inorganic and organic sludge. The simulated wastes for the test were formulated in the STAR Center. LIBS measurements were performed continuously at a port between the baghouse and the HEPA filter. To obtain good signal to noise, the typical sample integration time was 50 seconds in this test, this corresponds to averaging 500 laser pulses. The intensity of atomic emission lines observed in the LIBS spectrum was used to infer the concentration of the atomic species using calibration data obtained from a nebulizer. The EG&G OMA2000 software was used to collect LIBS data. A user-written macro program was employed to analyze and display the data in near real-time. The detector controller was also interfaced with the facility computer to provide information of the metal concentration levels. The concentrations of three elements versus time and the currently acquired LIBS spectrum are displayed on the computer screen. Moreover, the concentration of five selected species can be displayed at the bottom of the computer monitor during the data acquisition. TTL signals are sent to the alarm/interface system and a warning message is also shown on the bottom of the computer screen whenever the concentration of the probed species is above the alarm level during the LIBS measurements. This can allow the operator to modify operational parameters of the plasma system to prevent emissions that exceed the pre-established facility limits.

Five metals, Pb, Ni, Cr, Se, Hg, and Ce (as a nonradioactive surrogate for Pu) were preselected by the facility for real-time monitoring with LIBS. The spectral regions near 418 nm and 359 nm both cover five of the six desired metals and were selected to monitor the metal concentrations during this test. Calibration data of Ce, Cr, Pb, and Ni were collected in the DIAL laboratory with a nebulizer. The data recorded in the 418 nm spectral region showed that this spectral region can provide less interferences than in 359 nm spectral region. Data were collected in this spectral region for the rest of the test. The metals monitored in this spectral region are Pb, Ce, Cr, and Hg. Although there are some Se+ lines in this spectral regions, unfortunately, they are well below the detection limit and therefore were not monitored in this test. Unfortunately, there is an interference between the CN emission band and the Ce line in the 418 nm region; this reduced the accuracy of the inferred Ce concentrations. Therefore, the inferred Ce concentrations have an uncertainty of ~100 %. The concentration accuracies for Cr and Pb are estimated to be between 1 and 15% for concentrations above 100 µg/scm. The accuracies are estimated to be ~15–80% for concentrations below 100 µg/scm.

Most of the time, the metal emission is near or slightly above the LIBS detection limit. From time to time, metal emissions went up close to the alarm levels. It indicates there might be some problems in the plasma torch operation or in the baghouse at that particular moment. The TTL signals were successfully sent to the alarm/interface system when the concentrations went above the alarm limit.

DIAL's LIBS system has been used to record LIBS spectra of various elements in the off-gas streams at three thermal treatment facilities. The emission lines are calibrated to infer the concentration of the elements. These measurements show that LIBS can be used to monitor the concentration of selected toxic metals in the off-gas. In particular, the tests at various waste treatment facilities indicate that LIBS real time toxic metal measurements can be used as a process control monitor during hazardous waste processing. LIBS measurements at various locations in the off-gas emission can also provide information on operation of particular system components, such as the baghouse, HEPA filter, etc. Interfacing of LIBS with a waste treatment facility main computer can be used to control the waste treatment process for safe operation of the facility and also to satisfy the EPA compliance requirements for selected toxic metal emissions. For example, for plasma torch processing the air flow or the feed to the plasma torch can be automatically adjusted whenever the LIBS toxic metal concentration increases beyond a certain preassigned threshold limit.

obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A laser-induced breakdown spectroscopy apparatus comprising:

means for providing laser light;

a mirror harmonic separator;

a coated dichroic mirror;

a focusing lens system; and a detector, wherein laser light is directed via said mirror harmonic separator, said dichroic mirror and said focusing lens system onto a sample to be analyzed; and an emission spectrum of said sample is directed via said focusing lens system through said dichroic mirror to said detector.

2. The apparatus of claim 1, wherein said detector is an intensified diode array detector or an intensified charge couple device detector.

3. The apparatus of claim 1, wherein said dichroic mirror transmits wavelengths in the range of 180–1,000 nm, but reflects wavelengths from 500–540 nm, and said laser light is produced from an Nd:YAG laser.

4. The apparatus of claim 1, wherein said dichroic mirror is positioned at a 45° angle relative to a line between said detector and said sample to be analyzed.

5. The apparatus of claim 1, further comprising a doubling crystal.

6. The apparatus of claim 1, wherein said means for providing laser light is a pulsed laser selected from the group consisting of a $CO_2$, excimer krypton fluoride, neodymium yttrium-aluminum garnet, ruby, titanium sapphire, aluminum gallium arsenide, indium gallium arsenide phosphide, aluminum indium gallium phosphide, and dye lasers.

7. The apparatus of claim 1, wherein said focussing lens has a focal length of 100–1,000 mm.

8. The apparatus of claim 1, wherein said means for providing laser light has a pulse power density of $\geq 1$ $GW/cm^2$.

9. The apparatus of claim 1, wherein said means for providing laser light is a pulsed laser operating at a frequency of 5–30 Hz.

10. The apparatus of claim 1, wherein said means for providing laser light is a pulsed laser sending a pulse of 5–15 n sec.

11. The apparatus of claim 1, further comprising a fiber optic link between said focusing lens system and said detector.

12. The apparatus of claim 11, wherein said fiber optic link is a fiber optic bundle having a core diameter of 0.05 to 0.2 mm.

13. A method for analyzing composition of molten glass by laser-induced breakdown spectroscopy, comprising analyzing a sample of molten glass using: means for providing laser light, a mirror harmonic separator, a coated dichroic mirror, a focusing lens system, and a detector wherein laser light is directed via said mirror harmonic separator, said dichroic mirror and said focusing lens system onto a sample to be analyzed and including directing an emission spectrum of said sample via said focusing lens to said dichroic mirror to said detector.

14. An instrument for process control using: means for providing laser light, a mirror harmonic separator, a coated dichroic mirror, a focusing lens system, and a detector wherein laser lightis directed via said mirror harmonic separator, said dichroic mirror and said focusing lens system onto a sample to be analyzed and including directing an emission spectrum of said sample via said focusing lens to said dichroic mirror to said detector.

* * * * *

UNITED STATES PATENT AND TRADEMARK OFFICE
CERTIFICATE OF CORRECTION

PATENT NO. : 5,751,416
DATED : May 12, 1998
INVENTOR(S) : Jagdish P. Singh et al.

It is certified that error appears in the above-identified patent and that said Letters Patent is hereby corrected as shown below:

Column 1,
Line 2, after the title insert the following:

-- This invention was made with U.S. Government support under contract number DE-FG02-93CH10575 awarded by the Department of Energy. The U.S. Government may have certain rights in this invention. --

Signed and Sealed this

Fourth Day of December, 2001

*Attest:*

NICHOLAS P. GODICI
*Attesting Officer*    *Acting Director of the United States Patent and Trademark Office*